(12) United States Patent
Jyothi Prasad et al.

(10) Patent No.: US 7,960,545 B2
(45) Date of Patent: Jun. 14, 2011

(54) PROCESS FOR THE PREPARTION OF ERLOTINIB

(75) Inventors: Ramanadham Jyothi Prasad, Hyderbad (IN); Bollepalli Nageshwar Rao, Hyderbad (IN); Nannapaneni Venkaiah Chowdary, Hyderbad (IN)

(73) Assignee: Natco Pharma Limited, Andhra Pradesh (IN)

( * ) Notice: Subject to any disclaimer, the term of this patent is extended or adjusted under 35 U.S.C. 154(b) by 267 days.

(21) Appl. No.: 12/094,926

(22) PCT Filed: Nov. 22, 2006

(86) PCT No.: PCT/IN2006/000464
§ 371 (c)(1),
(2), (4) Date: Oct. 16, 2008

(87) PCT Pub. No.: WO2007/060691
PCT Pub. Date: May 31, 2007

(65) Prior Publication Data
US 2009/0306377 A1 Dec. 10, 2009

(30) Foreign Application Priority Data
Nov. 23, 2005 (IN) .......................... 1715/CHE/2005

(51) Int. Cl.
*C07D 239/72* (2006.01)
(52) U.S. Cl. .................................................... 544/293
(58) Field of Classification Search ................... 544/293
See application file for complete search history.

(56) References Cited

U.S. PATENT DOCUMENTS

| 5,747,498 A | 5/1998 | Schnur et al. |
| 6,900,221 B1 | 5/2005 | Norris et al. |

FOREIGN PATENT DOCUMENTS

| WO | WO 96/09294 | 3/1996 |
| WO | WO 96/30347 | 10/1996 |
| WO | WO 01/34574 | 5/2001 |

*Primary Examiner* — James O. Wilson
*Assistant Examiner* — Brian McDowell
(74) *Attorney, Agent, or Firm* — Merchant & Gould P.C.

(57) ABSTRACT

The present invention discloses an improved and novel process for the preparation of erlotinib (N-(3-ethynylphenyl)-6,7-bis(2-methoxyethoxy)-4-quinazolinamine) of formula (1), which comprises: (i) demethylation of commercially available 6,7-dimethoxy-4(3H)-quinazolinone of formula (8); acetylation using acetic anhydride; (iii) introduction of a leaving group at C-4 position in quinazolinone; (iv) condensation with 3-ethynylaniline to get novel compound of formula (12); (v) deacetylation to get novel dihydroxy compound of formula (13); and (vi) O-alkylation with 2-iodoethylmethyl ether to get the erlotinib base of formula (1). Erlotinib base is purified by recrystallization from ethyl acetate to get a HPLC purity of >99.5%. Salt formation of this base with hydrogen chloride gave pharmaceutically acceptable erlotinib hydrochloride of formula (1a) with a HPLC purity of >99.8%. Erlotinib hydrochloride is useful for the treatment of proliferative disorders, such as cancers, in humans.

31 Claims, No Drawings

PROCESS FOR THE PREPARTION OF ERLOTINIB

The present invention relates to a novel process for the preparation of Erlotinib of formula-(1) whose chemical name is N-(3-ethynylphenyl)-6,7-bis(2-methoxyethoxy)-4-quinazolinamine, and its pharmaceutically acceptable salts thereof. Erlotinib is an inhibitor of the erbB family of oncogenic and protooncogenic protein tyrosine kinases, such as epidermal growth factor (EGFR) and is therefore useful for the treatment of proliferative disorders, such as cancers, in humans.

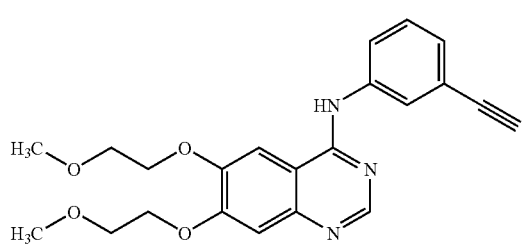

(1)

The present invention is related to the process for Erlotinib of formula (1), starting from 6,7-dimethoxy-4(3H)-quionazolinone involving novel intermediates N-(3-ethynylphenyl)-6,7-diacetoxy-4-quinazolinamine and its acid addition salts and N-(3-ethynylphenyl)-6,7-dihydroxy-4-quinazolinamine.

BACKGROUND OF INVENTION

Erlotinib of formula (1) is first reported by Schnur, Rodney.C. (Pfizer Inc. NY. US) in PCT International Publication WO.96/30347 (1996) US equivalent is U.S. Pat. No. 5,747,498 (1998).

The process for the preparation of Erlotinib disclosed in WO 96/30347 is shown in Scheme-1. The starting material Ethyl-3,4-dihydroxy benzoate of formula (2) is reacted with 2-bromo ethylmethyl ether in presence of a base to obtain bis-O-alkylated compound of formula (3), which is nitrated on ortho position with nitric acid in acetic acid medium to get 2-Nitro-4,5-bis(2-methoxyethoxy)benzo ate of formula (4). The nitro compound of formula (4) on hydrogenation using platinum oxide hydrate gives the amino compound of formula (5), which further reacted with ammonium formate and formamide to get 4-quinazolone compound of formula (6). The 4-quinazolone derivative is reacted with oxalyl chloride to get 4-chloro quinazoline derivative of formula (7), which on condensation with 3-ethynylaniline gives a residue containing Erlotinib base of formula (1). The residue thus obtained is purified by flash chromatography on silica to get Erlotinib base. Then the base is converted to its hydrochloride salt.

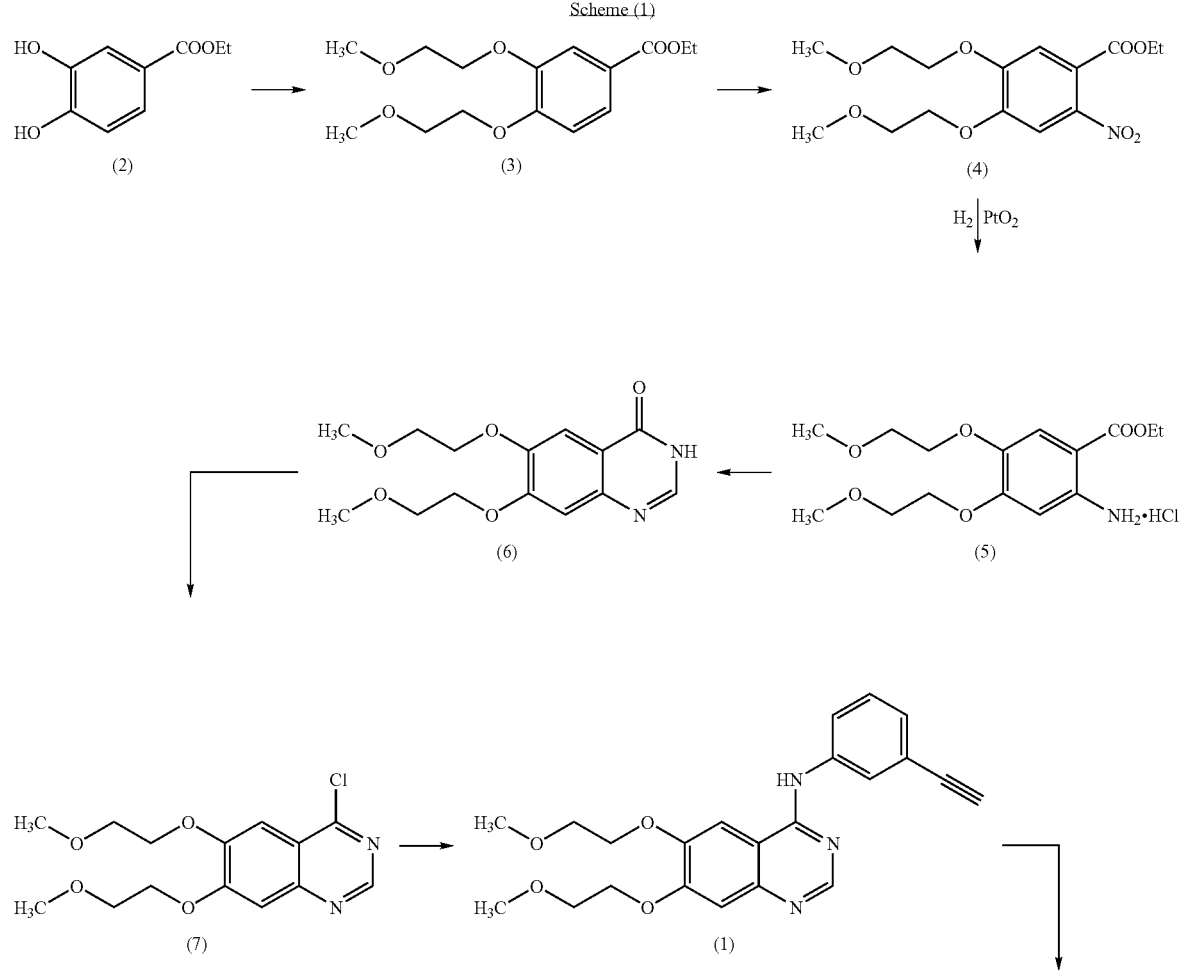

Scheme (1)

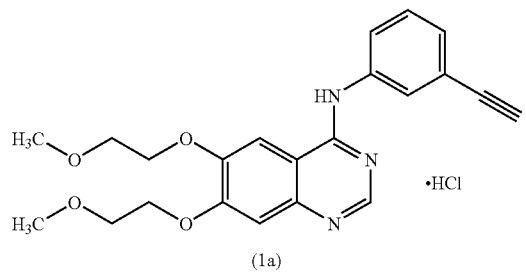

(1a)

In the subsequent patent WO 01/34574 and its equivalent U.S. Pat. No. 6,900,221 B1 a process for the preparation of stable form of erlotinib hydrochloride of formula (1a) is disclosed as shown in Scheme 2 below.

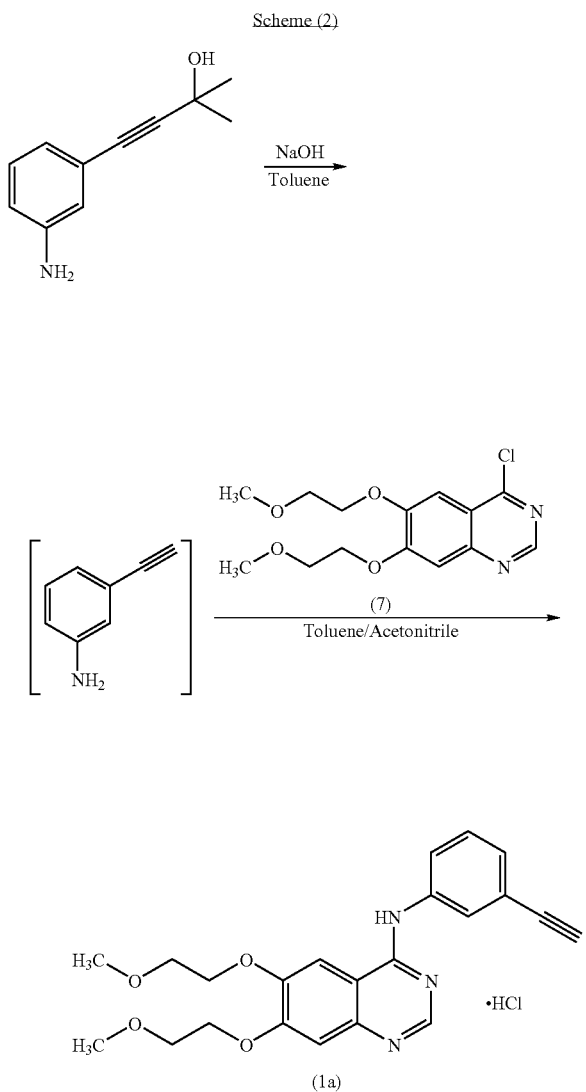

The main disadvantages in the above said patents are:
1. During the nitration of compound (3), we observed that the reaction is scale dependent. With increase in scale, yield and quality of the product decreased.
2. A highly expensive platinum oxide is used in the catalytic hydrogenation step, which also requires special equipment to carryout hydrogenation.
3. The chemistry applied to get the erlotinib compound in the patent WO 01/34574 is same as that given in the basic patent WO 96/30347 except the base is purified by flash chromatography in the basic patent. So the disadvantages are same in both the patents
4. Yield and quality of the final product is not disclosed in both the patents.

So the above-mentioned processes are not economically viable

SUMMARY OF INVENTION

Keeping in view of the difficulties in the above-described process for the preparation of Erlotinib of formula (1) on a commercial scale, we aimed to develop a simple and economically viable and commercially applicable process for the preparation of Erlotinib.

Accordingly, the main objective of the present invention is to provide an improved process for the preparation of Erlotinib of formula-(1), which is simple and economical and commercially applicable.

According to another objective of the present invention is to provide an improved process for the preparation of Erlotinib of formula-(1), which involves readily and cheaply available raw materials.

During our elaborate research in developing a process for the preparation of Erlotinib of formula (1) on a commercially viable scale, we observed that commercially and readily available 6,7-dimethoxy-4(3H)-quinazolinone could be a suitable starting material, when compared to ethyl 3,4-dihydroxy benzoate used in the prior art.

Accordingly, the basic raw material selected for the synthesis of Erlotinib of formula (1) is 6,7-dimethoxy-4(3H)-quinazolinone of formula (8). The process is as outlined in Scheme (3).

The key intermediate 6,7-diacetoxy-4(1H)-quinazilinone-hydrobromide is reported in WO 96/09294 (Wellcome foundation, GB), starting from 6,7-dimethoxy-4(1H)-quinazolinone, through 6,7-dihydroxy-4(1H)-quinazilinone hydrobromide. The yield reported for 6,7-dihydroxy compound is 92% and from this to 6,7-diacetoxy compound is 75% yield. The purity of these two intermediates is not reported.

Scheme (3)

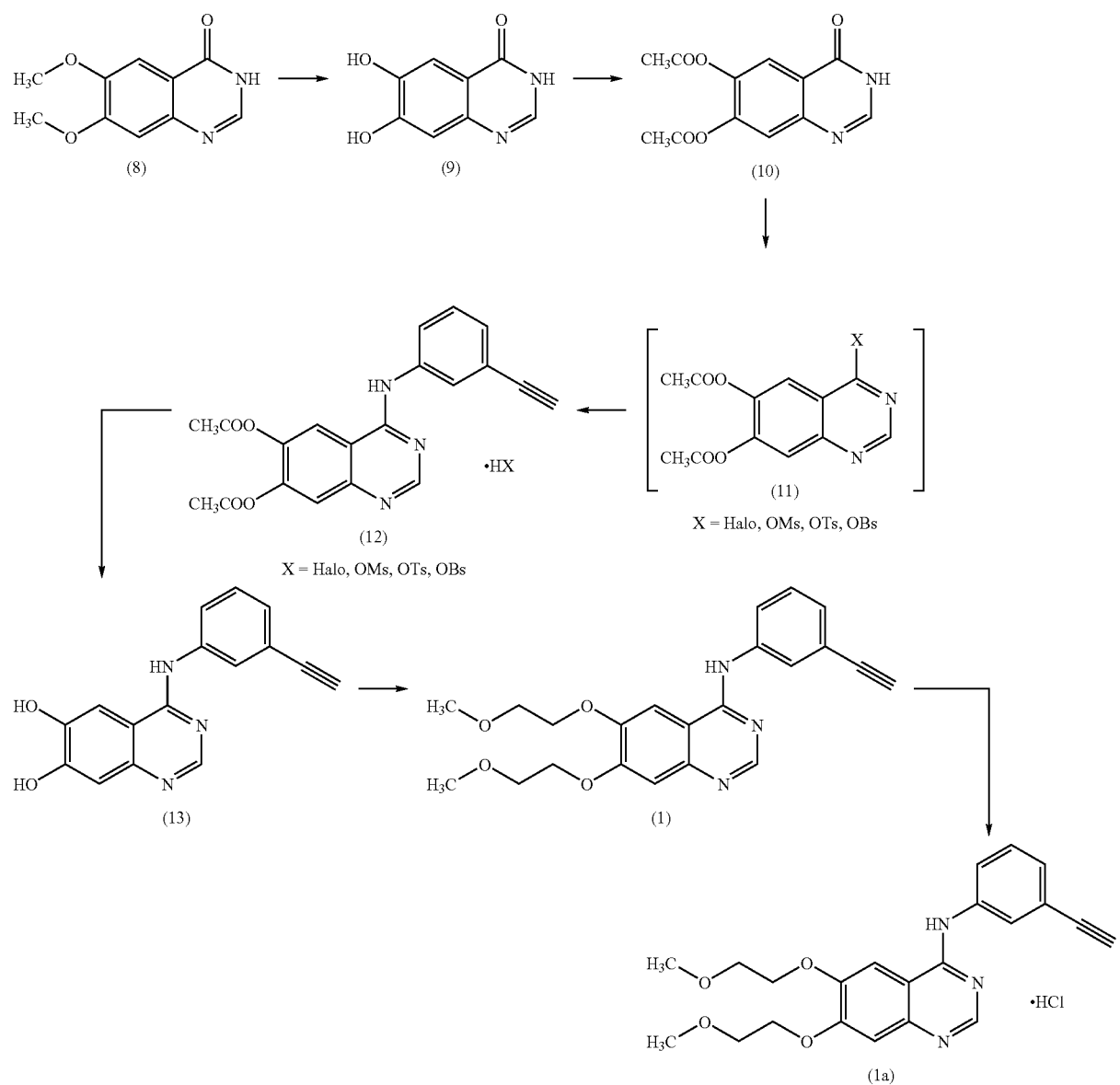

We have now improved the process for 6,7-dihydroxy-4 (3H)-quinazolinone (as base) from 6,7-dimethoxy-4(3H)-quinazolinone by using 48% hydrobromic acid instead of 38% hydrobromic acid as mentioned in WO 96/09294, with 98.62% yield and 99.5% purity by HPLC. We could also reduce the molar equivalents of hydrobromic acid used in this process. Accordingly our process requires 26 molar equivalents of hydrobromic acid as compared to 46 molar equivalents used in the prior art process. We also improved the process in acetylation stage using reduced quantity of acetic anhydride compared to the process disclosed in WO 96/09294. Process disclosed in WO 96/09294 uses 275 equivalents of acetic anhydride compared to 15 equivalents of our process. We could achieve this by using a catalyst such as pyridine or 4-dimethylaminopyridine. Yield of 6,7-diacetoxy-4(3H)-quinazolinone of formula (10) is 92.5% (by theory) with a purity of 99% by HPLC. Accordingly, the invention provides an improved process for the preparation of compound of formula (1)

and its pharmaceutically acceptable salts, which comprises, (i) reacting 6,7-dimethoxy-4(3H)-quinazolinone of formula (8)

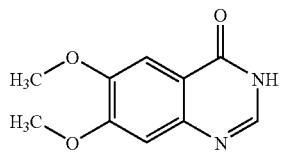
(8)

with aqueous hydrobromic acid or pyridine hydrochloride at elevated temperature to get a hydrobromide or hydrochloride salt of dihydroxy compound which on neutralization with a base to get the compound of formula (9)

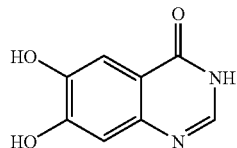
(9)

(ii) acylating the compound of formula (9) using an acylating agent at a temperature in the range of 20-150° C. and in the presence of a catalyst to get the bis-acylated derivative of formula (10).

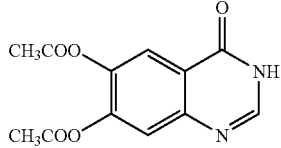
(10)

(iii) converting the keto group present in the compound of the formula (10) in to a leaving group 'X' by using an appropriate reagent in the presence or absence of a solvent at a temperature of 10-100° C. to get the compound of the formula (11)

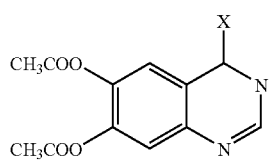
(11)

X=Halo, OMs, OTs, OBs (iv) condensing the reaction mass containing the crude compound of formula (11) with 3-ethynylaniline in an organic solvent at a temperature of 10-100° C. to get a novel compound of compound of formula (12),

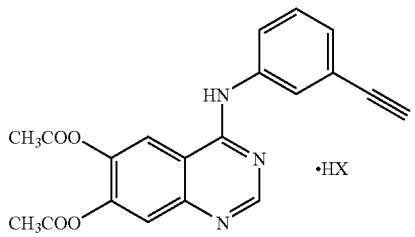
(12)

Wherein X=Halo, OMs, OTs, OBs (v) reacting the compound of the formula (12) with a base at a temperature of 20-60° C. to get the novel deacylated compound of the formula (13),

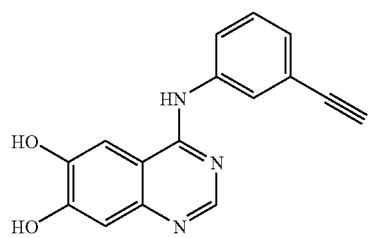
(13)

(vi) reacting the compound of the formula (13) with 2-halo-ethylmethyl ether in the presence of a base at a temperature of 25-100° C. to get the crude erlotinib base of the formula (1),

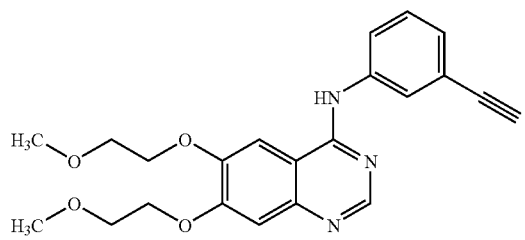
(1)

(vii) recrystallising of crude erlotinib base of formula (1) from different solvents to get pure erlotinib base
(viii) reacting pure Erlotinib base of formula (1) by dissolving or suspending in an organic solvent or water or a mixture thereof with aqueous hydrochloric acid or hydrogen chloride gas dissolved in an organic solvent to get high purity (>99.8% by HPLC) Erlotinib hydrochloride of formula (1a)

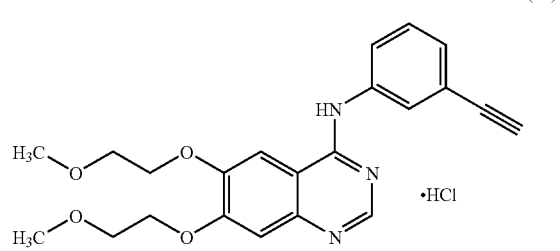
(1a)

DETAILED DESCRIPTION OF INVENTION

In a preferred embodiment of the present invention,

In the first step, 6,7-dimethoxy-4(3H)-quinazolinone of formula (8) is reacted with aqueous hydrobromic acid or pyridine hydrochloride to get the compound of formula (9). The percentage of hydrobromic acid can be between 30-60%, preferably 40-50% most preferably 46-48%. Temperature of the reaction is between 80-150° C. preferably 110-125° C. The compound of the formula (9) can be isolated from its hydrobromide salt by neutralization with a base to neutral pH. The base used in neutralization can be an inorganic base or organic base. The inorganic base is selected from sodium or potassium hydroxide, carbonate, hydrogen carbonate. The organic base is selected from aqueous ammonia, ethylamine, propylamine, diethylamine, triethylamine, pyridine etc preferably aqueous ammonia. The neutralization pH is in the range of 6.5-7.5 preferably 7.0-7.5.

In the second step, the dihydroxy compound of the formula (9) is acylated to get a bis-acylated compound of the formula (10). The acylating agent is selected from acetic anhydride, acetyl chloride etc. preferably acetic anhydride. The catalyst used for acylation is pyridine or 4-dimethylaminopyridine. Temperature of the reaction is between 80-150° C. preferably 120-130° C.

In the third step, conversion of the keto group present in the formula (10) in to a leaving group 'X' present in compound of the formula (11) can be done by treating the compound of the formula (10) with reagents such as thionyl chloride, phosphorous pentachloride, phosphorous oxychloride, oxalyl chloride, methanesulfonyl chloride, benzenesulfonyl chloride, para-toluenesulfonyl chloride etc. preferably thionyl chloride, oxalyl chloride, phosphorous oxy chloride or methanesulfonyl chloride in the absence or presence of a solvent. The solvent employed in the reaction is selected from methylene chloride, chloroform, toluene, acetonitrile, cyclohexane, preferably chloroform or methylene chloride or cyclohexane. Preferred temperature of the reaction is between 60-80° C. and most preferably 60-65° C. The product thus obtained can be directly used in the next step without isolation from the solvent and without any purification.

In the fourth step, the condensation of 3-ethynylaniline with the compound of the formula (11) to get the compound of the formula (12) can be done by reacting the compound of the formula (11) in the solvent medium at a temperature in the range of 25-160° C. The preferred solvent used can be selected from chloroform, methylene chloride, acetonitrile, isopropyl alcohol, toluene, tetrahydrofuran, dioxane, cyclohexane, dimethylformamide preferably chloroform, acetonitrile or isopropyl alcohol. The temperature of the reaction is in between 25-160° C. preferably 60-80° C.

In the fifth step, deacylation of the compound (12) to get the compound of the formula (13) can be done by reacting with bases such as aqueous sodium or potassium hydroxides, or aqueous ammonia solution in alcohols preferably aqueous methanolic ammonia. The temperature of the reaction can be in the range of 20-60° C. preferably 25-35° C.

In the sixth step, the compound of the formula (13) is reacted with 2-halo-ethylmethylether in the presence of a base to get the bis-O-alkylated compound of the formula (1). The 2-halo-ethylmethyl ether used in the alkylation step can be selected from chloro, bromo, or iodo derivative preferably iodo or bromo compound. The base used in the reaction can be an inorganic base such sodium or potassium carbonate, sodium hydride. Alternatively the base used in the alkylation step can be an organic base such as diisopropyl ethyl amine, triethylamine, pyridine, DBU (diazabicyclo[5.4.0]undec-7-ene), DABCO (1,4-Diazabicyclo[2.2.2]octane, etc. The solvent used in the reaction can be selected from dimethylformamide, acetonitrile, tetrahydrofuran, acetone, dimethylacetamide, isopropyl alcohol preferably dimethylformamide or acetonitrile. The temperature of the reaction is between 25-100° preferably 40-60° C. and most preferably 45-50° C.

The Erlotinib base thus obtained is purified by recrystallization from different solvents like Ethyl acetate, acetonitrile, isopropyl alcohol, methanol, ethanol, acetone, methyl ethyl ketone, water or a mixture thereof. Preferably ethyl acetate, acetonitrile and isopropyl alcohol and most preferably ethyl acetate. The isolation temperature of recrystallized erlotinib base is 0-25° C., preferably 0-5° C.

The erlotinib base obtained according to the process of present invention is more than 99.5% purity by HPLC.

The purified Erlotinib base thus obtained can be converted into monohydrochloride salt by suspending or dissolving the Erlotinib base in water or an organic solvent or a mixture of organic solvents and then treating with aqueous hydrochloric acid or hydrogen chloride gas dissolved in an organic solvent. The organic solvent used for dissolving or suspending the erlotinib base is selected from chloroform, toluene, ethanol, methanol, isopropyl alcohol, acetone, methyl ethyl ketone, acetonitrile, ethyl acetate, dimethylformamide, dimethyl ether, diethyl ether, tetrahydrofuran. The organic solvent used for dissolving hydrogen chloride gas is selected from ethanol, methanol, isopropyl alcohol, ethyl acetate, diethyl ether, dimethyl ether. The temperature of the reaction during hydrochloride salt formation and isolation is between 0-80° C.

The erlotinib hydrochloride obtained according to the process of present invention is more than 99.8% purity by HPLC.

The details of the invention are given in the examples below which are provided to illustrate the invention only and therefore should not be construed to limit the scope of the present invention.

EXAMPLE-1

Preparation of N-(3-ethynylphenyl)-6,7-bis(2-methoxyethoxy)-4-quinazolinamine (Erlotinib Base)

(i) Preparation of 6,7-dihydroxy-4(3H)-quinazolinone of formula (9)

Into a 2.0 Lt four necked round bottomed flask equipped with a mechanical stirrer, reflux condenser and thermometer socket are charged 48% (w/w) hydrobromic acid (1000 g) and 6,7-dimethoxy-4(3H)-quinazolinone (100 g). Slowly heated the reaction mass to reach 110° C. and maintained for 1 hour at the same temperature. Then raised mass temperature to reach reflux condition and refluxed for 12 hours. Monitored the completion of the reaction by TLC. Then cooled the reaction mass to 25-35° C. and filtered the mass. Transferred the wet cake into another 2.0 Lt round bottomed flask containing 1000 ml of DM water. Stirred for 10-15 minutes and adjusted the pH to 7.0-7.5, by adding aqueous ammonia solution. Filtered the resulting product and washed the cake with DM water and dried to get 85.2 g (98.62% by theory) of 6,7-dihydroxy-4(3H)-quinazolinone as off-white crystalline solid.

Purity: 99.25% (by HPLC)

Melting point: >250° C.

IR (KBr): 3208.7, 1679.0, 1614.5, 1514.7, 1427.7, 1374.3, 1316.2, 1293.9, 1261.0, 1214.5, 1195.5, 866.0, 845.3, 780.7, 523.8, and 449.2 cm$^{-1}$ $^1$H NMR (300 MHz, DMSO-D$_6$): 6.93 (s, 1H); 7.35 (s, 1H); 7.84 (s, 1H); 9.75 (s, 1H); 10.13 (s, 1H); 11.2-12.4 (s, 1H)

Mass: 179 (M+1), 177 (M−1)

(ii) Preparation of 6,7-diacetoxy-4(3H)-quinazolinone of formula (10)

Into a 1.0 L four necked round bottomed flask equipped with a mechanical stirrer, reflux condenser and thermometer socket are charged acetic anhydride (600 g), pyridine (4 ml) followed by 6,7-dihydroxy-4(3H)-quinazolinone (100 g) obtained by the process described in step (i) above. The reaction mass was heated to 120° C. and maintained for 2 hours at 120-125° C. After completion of the maintenance period, distilled off the solvent under vacuum. Cooled the reaction mass to 25-35° and water (1000 ml) was added, stirred for 1 hour, filtered the product and washed the cake with water and dried to get 136.2 g (92.5% by theory) of 6,7-diacetoxy-4(3H)-quinazolinone as off-white crystalline solid.

Purity: 99.0% (by HPLC)
Melting range: 235-237° C.
IR ((KBr): 3128, 3044, 2930, 2882, 1779, 1693, 1660, 1620, 1479, 1372, 1280, 1209, 1163, 929, and 914 cm$^{-1}$
$^1$H NMR (300 MHz, DMSO-d$_6$): 2.3-2.32 (s, 6H); 7.58 (s, 1H); 7.95 (s, 1H); 8.12 (d, 1H); 12.39 (br. s, 1H)
$^{13}$C NMR (75 MHz, DMSO-d$_6$): 20.14, 20.31, 115.8, 118.5, 124, 140.9, 144.2, 145.7, 150.1, 160.4, and 168.6
Mass: (M+1): 263

(iii) Preparation of 4-Chloro-6,7-diacetoxy-quinazoline of formula (11) (X=Cl)

Into a 3.0 L four necked round bottomed flask, equipped with a mechanical stirrer, reflux condenser, pressure equalizing addition funnel and thermometer socket are charged chloroform (1000 ml), 6,7-diacetoxy-4(3H)-quinazolinone (50 g) obtained by the process described in step (ii) above and dimethylformamide (2 ml). Oxalyl chloride (50 g) was slowly added in about 20-30 minutes. The reaction mass was slowly heated to reflux temperature and maintained at reflux temperature for 6 hours. Reaction was found to be over by HPLC. Cooled the reaction mass to 25-30° C. and slowly quenched into saturated sodium bicarbonate solution at less than 10° C. Separated the organic layer and dried over anhydrous sodium sulfate. The dried organic layer thus obtained was directly used in the next step without any purification.

A small sample was isolated from the above solution and was characterized.

MR: 111-115° C.
IR (KBr): 1176.9, 1626.3, 1554.7, 1484.0, 1400.5, 1373.1, 1348.5, 1259.0, 1194.6, 1131.5, 1016.2, 920.9, 880.6, 803.6, and 702.4 cm$^{-1}$.
$^1$H NMR (300 MHz, DMSO-d$_6$): 2.31-2.33 (s, 6H), 7.64 (s, 1H); 7.98 (s, 1H); 8.37 (s, 1H)
$^{13}$C NMR (75 MHz, DMSO-d$_6$): 20.43, 20.46, 118.29, 120.25, 121.04, 141.07, 141.88, 147.53, 148.03, 158.91, 167.84, and 168.24.
Mass: 281 (M+1).

(iv) Preparation of N-(3-ethynylphenyl)-6,7-diacetoxy-4-quinazolinamine hydrochloride of formula (12) (X=Cl)

Into a 2.0 Lt four-necked round-bottomed flask, equipped with a mechanical stirrer, reflux condenser and thermometer socket are charged the organic layer from the previous stage (Step 3) containing 4-Chloro-6,7-diacetoxy-quinazoline and 3-ethynylaniline (20 g). The reaction mass was slowly heated to reach reflux condition and maintained and reflux for 14 hours and the reaction was found to be over by HPLC. Then the reaction was cooled to 25-30° C. and filtered the mass washed the cake with chloroform and dried to get 60 g (79% by theory) of N-(3-ethynylphenyl)-6,7-diacetoxy-4-quinazolinamine hydrochloride as yellow solid.

Purity: 96.76% (by HPLC).
Melting Range: 216-223° C.
IR (KBr): 3290, 3012, 2613, 1775, 1639, 1616, 1564, 1539, 1485, 1443, 1373, 1280, 1194, 1131, 1059, 1014, and 787 cm$^{-1}$.
$^1$H NMR (300 MHz, DMSO-d$^6$): 2.38 (s, 3H); 2.41 (s, 3H); 4.28 (s, 1H); 7.40-7.41 (d, 1H); 7.48-7.51 (m, 1H); 7.77-7.78 (d, 1H); 7.91 (s, 2H); 8.88 (s, 1H); 8.93 (s, 1H); 11.45 (br s, 1H).
$^{13}$C NMR (75 MHz, DMSO-d$_6$): 20.13, 20.53, 81.33, 82.86, 105.9, 112.03, 119.03, 119.77, 122.01, 120.04, 125.04, 125.17, 129.19, 140.51, 141.88, 148.11, 157.45, 158.91, 168.24, 168.41
Mass: 362 (M+1).

(v) Preparation of N-(3-ethynylphenyl)-6,7-hydroxy-4-quinazolinamine of formula (13)

Into a 500 ml, three necked round bottomed flask equipped with a mechanical stirrer and thermometer socket are charged methanol (150 ml), aqueous ammonia solution (25% w/w) (55 g) and N-(3-ethynylphenyl)-6,7-diacetoxy-4-quinazolinamine hydrochloride (50 g) obtained by the process described in step (iv) above. Maintained the reaction mass under stirring for 4 hours at 25-30° C. and the reaction was found to be over by TLC. Filtered the reaction mass and washed the cake with methanol and dried to get 34 g (97.6% by theory) of N-(3-ethynylphenyl)-6,7-hydroxy-4-quinazolinamine as a brownish yellow solid.

Purity: 99.0% (by HPLC).
Melting point: >250° C.
IR (KBr): 3299, 1615, 1572, 1534, 1456, 1390, 1298, 1223, 1166, 949, 847, 792, 647, and 592 cm$^{-1}$
$^1$H NMR (300 MHz, DMSO-d$_6$): 3.76 (s, 1H); 4.1 (s, 2H); 6.8 (s, 1H); 7.08-7.10 (d, 1H); 7.29-7.31 (t, 1H); 7.76 (s, 1H); 7.89-7.91 (d, 1H); 8.08 (s, 1H); 8.29 (s, 1H); 8.8-9.4 (br s, 1H)
$^{13}$C NMR (75 MHz, DMSO-d$_6$): 80.14, 84.0, 101.74, 106.39, 108.12, 121.60, 123.74, 125.22, 128.74, 140.96, 147.41, 149.86, 150.87, 155.40, and 159.09.
Mass: 278 (M+1).

(vi) Preparation of N-(3-ethynylphenyl)-6,7-bis(2-methoxyethoxy)-4-quinazolinamine (Erlotinib base) of formula (1)

Into a 2.0 L four necked round bottomed flask equipped with a mechanical stirrer, reflux condenser, thermometer socket, are charged dimethylformamide (1250 ml), anhydrous potassium carbonate (150 g), N-(3-ethynylphenyl)-6,7-hydroxy-4-quinazolinamine (50 g) obtained from the process described in step (v) above. To the reaction mixture, 2-iodo-ethylmethyl ether (70 g) was added in about 10-15 minutes. Then slowly raised the temperature to 45° and maintained for 12 hours at 45-50° C. and the reaction was found to be over by HPLC. Then cooled the reaction mass to 30-35° C. and filtered to remove the inorganic salt. Washed the cake with DMF. The solvent was removed by distillation under reduced pressure. Cooled the reaction mass to 30-35° C. and extracted the product by the addition of water and methylene chloride. The organic layer was separated and washed with water and dried over sodium sulfate. The solvent was removed under reduced pressure to get the residue which was triturated with toluene and the product was obtained by filtration and dried to get crude erlotinib base (N-(3-ethynylphenyl)-6,7-bis(2-methoxyethoxy)-4-quinazolinamine) (42 g) (59.1% by theory) as a light yellow colored crystalline solid.

Purity: 99% (by HPLC).
Melting range: 151-153° C.

(vii) Recrystallization of Erlotinib Base

Into a 1.0 L four necked round bottomed flask equipped with a mechanical stirrer, reflux condenser and thermometer socket, are charged ethyl acetate (480 ml), Erlotinib base (40 g) obtained by the process described in step (vi) above and slowly raised the temperature to 75-80° C. to dissolve the base completely. Then activated carbon (6 g) was charged and maintained for 15-20 minutes. Filtered and washed the carbon cake with hot ethyl acetate. The combined filtrate and washings were cooled to 25-30° C. and then cooled further to 0-5° C. The reaction mass was maintained at 0-5° C. for 1 hour, filtered, washed with chilled ethyl acetate and dried to get 36 g of pure erlotinib base of formula (1) as light yellow colored crystalline solid.

MR: 154-155° C.
Purity: 99.65% (by HPLC).
IR (KBr): 3250, 2927, 1619, 1576, 1502, 1428, 1332, 1255, 1217, 1153, 1130, 1094, 1066, 1032, 979, 940, 849, 770, 662, and 588 cm$^{-1}$
$^1$H NMR (300 MHz, DMSO-$d_6$): 3.29 (s, 6H); 3.73 (t, 4H); 3.92 (s, 1H); 4.11-4.21 (m, 4H); 7.14 (s, 1H); 7.38-7.48 (m, 2H); 7.53-7.75 (dd, 1H); 7.86 (s, 1H); 8.37 (s, 1H); 8.84 (s, 1H); 11.44 (s, 1H).
$^{13}$C NMR (75 MHz, DMSO-$d_6$): 58.37, 68.60, 69.17, 69.66, 69.90, 81.09, 82.91, 100.28, 105.02, 107.12, 121.77, 125.19, 127.42, 128.78, 129.03, 135.16, 137.16, 148.19, 149.12, 155.30, 157.70
Mass: 394 (M+1)

EXAMPLE 2

Preparation of N-(3-ethynylphenyl)-6,7-bis(2-methoxyethoxy)-4-quinazolinamine hydrochloride (Erlotinib hydrochloride) of formula (1a)

Into a 1.0 L four necked round bottomed flask equipped with a mechanical stirrer, reflux condenser and thermometer socket, are charged Isopropyl alcohol (600 ml), Erlotinib base (30 g) obtained by the process described in step (vii) of example (1) and slowly raised the temperature to 75-80° C. to dissolve completely. Then activated carbon (6 g) was charged and maintained for 15-20 minutes. Filtered and washed the carbon cake with hot isopropyl alcohol. The combined filtrate and washings were cooled to 40-45° C. then isopropyl alcohol-HCl (1.1 molar equivalent) was slowly added in about 10-15 minutes. Raised the temperature to 60-65° C. and maintained for 1 hour. Cooled to 25-30° C. and filtered the product and washed the cake with Isopropyl alcohol and dried to get 30.5 g (93.2% by theory) of Erlotinib monohydrochloride as a white solid.

Purity: 99.8% (by HPLC).

EXAMPLE 3

Preparation of N-(3-ethynylphenyl)-6,7-diacetoxy-4-quinazolinamine hydrochloride of formula (12) (X=Cl)

Into a 3.0 L four necked round bottomed flask, equipped with a mechanical stirrer, reflux condenser, pressure equalizing addition funnel and thermometer socket are charged chloroform (500 ml), 6,7-diacetoxy-4(3H)-quinazolinone (25 g) obtained from the process described in step (ii) of example (1) and dimethylformamide (3 ml). Thionyl chloride (46.2 g) was slowly added in about 20-30 minutes. The reaction mass was slowly heated to reflux temperature and maintained at reflux temperature for 6 hours. Reaction was found to be over by HPLC. Cooled the reaction mass to 25-30° C. and slowly quenched into saturated sodium bicarbonate solution at less than 10° C. Separated the organic layer and dried over anhydrous sodium sulfate. The dried organic layer containing 4-chloro-6,7-diacetoxyquinozoline (11) (X=Cl) thus obtained was directly used in the next step without purification.

Into a 2.0 L four necked round-bottomed flask, equipped with a mechanical stirrer; reflux condenser and thermometer socket are charged the above organic layer containing 4-chloro-6,7-diacetoxy-quinazoline and 3-ethynylaniline (12 g). The reaction mass was slowly heated to reach reflux condition and maintained at reflux for 14 hours and the reaction was found to be over by HPLC. Then the reaction was cooled to 25-30° C. and filtered the mass, washed the cake with chloroform, and dried to get 29 g (76.3% by theory) of N-(3-ethynylphenyl)-6,7-diacetoxy-4-quinazolinamine hydrochloride as yellow solid.

Purity: 96.1% (by HPLC).
The spectral data is in concordance with the sample obtained as in step (iv) of Example (1).

EXAMPLE 4

Preparation of N-(3-ethynylphenyl)-6,7-diacetoxy-4-quinazolinamine hydrochloride of formula (12) (X=Cl)

Into a 3.0 Lt four necked round bottomed flask, equipped with a mechanical stirrer, reflux condenser, pressure equalizing addition funnel and thermometer socket are charged chloroform (500 ml), 6,7-diacetoxy-4(3H)-quinazolinone (25 g) obtained from the process described in step (ii) of example (1) and dimethylformamide (3 ml). Thionyl chloride (46.2 g) was slowly added in about 20-30 minutes. The reaction mass was slowly heated to reflux temperature and maintained at reflux temperature for 6 hours. Reaction was found to be over by HPLC. Cooled to 45-50° C. then added chloroform (500 ml) and distilled out 500 ml of chloroform. Repeated the distillation process another two times with fresh chloroform. Then cooled the reaction mass to 20° C. 3-Ethynylaniline (15 g) was added and maintained for 2-3 hours at 20-25° C. Completion of the reaction is monitored by HPLC. Distilled of the solvent completely under vacuum. Cooled the reaction mass to 20-25° C. and triturated with isopropyl alcohol and filtered and washed the cake with isopropyl alcohol and dried to get N-(3-ethynylphenyl)-6,7-diacetoxy-4-quinazolinamine hydrochloride 28 g (73.6% by theory).

Purity: 95.27% (by HPLC)

The spectral data is in concordance with the sample obtained as in step (iv) of Example (1).

EXAMPLE 5

Preparation of Erlotinib Monohydrochloride of Formula (1a)

Into a 500 ml four necked round bottomed flask equipped with a mechanical stirrer, reflux condenser and thermometer socket, are charged acetone (250 ml), Erlotinib base (10 g) and stirred at 30-35° C. to get a clear solution. Then activated carbon (2 g) was charged and maintained for 15-20 minutes. Filtered and washed the carbon cake with Acetone. To the combined filtrate and washings was added isopropyl alcohol-HCl (1.1 molar equivalent) slowly added in about 10-15 minutes. Raised the temperature to 50-55° C. and maintained for 1 hour. Cooled to 25-30° C. and filtered the product and washed the cake with acetone and dried to get 10.1 g (92.6% by theory) of Erlotinib monohydrochloride as a white solid.

Purity: 99.81% (by HPLC)

EXAMPLE 6

Preparation of Erlotinib Monohydrochloride

Into a 250 ml four necked round bottomed flask equipped with a mechanical stirrer, reflux condenser and thermometer socket, are charged dimethylformamide (100 ml), Erlotinib base (10 g) and stirred at 30-35° C. to get a clear solution. Then activated carbon (2 g) was charged and maintained for 15-20 minutes. Filtered and washed the carbon cake with dimethylformamide. To the combined filtrate and washings was added isopropyl alcohol-HCl (1.1 molar equivalent) slowly added in about 10-15 minutes. Raised the temperature to 70-75° C. and maintained for 1 hour. Cooled to 25-30° C. and filtered the product and washed the cake with Isopropyl alcohol and dried to get 10.0 g (91.5% by theory) of Erlotinib monohydrochloride as a white solid.

Purity: 99.82% (by HPLC).

EXAMPLE 7

Preparation of Erlotinib Monohydrochloride

Into a 500 ml four necked round-bottomed flask equipped with a mechanical stirrer, reflux condenser and thermometer socket, are charged Tetrahydrofuran (200 ml), Erlotinib base (10 g) and stirred at 30-35° C. to get a clear solution. Then activated carbon (2 g) was charged and maintained for 15-20 minutes. Filtered and washed the carbon cake with Tetrahydrofuran. To the combined filtrate and washings was added isopropyl alcohol-HCl (1.1 molar equivalent) slowly added in about 10-15 minutes. Raised the temperature to 60-65° C. and maintained for 1 hour. Cooled to 25-30° C. and filtered the product and washed the cake with tetrahydrofuran and dried to get 10.2 g (93.4% by theory) of Erlotinib monohydrochloride as a white solid.

Purity: 99.82% (by HPLC)

EXAMPLE 8

Preparation of Erlotinib Monohydrochloride

Into a 250 ml four necked round-bottomed flask equipped with a mechanical stirrer, reflux condenser and thermometer socket, are charged Chloroform (150 ml), Erlotinib base (10 g) and stirred at 30-35° C. to get a clear solution. Then activated carbon (2 g) was charged and maintained for 15-20 minutes. Filtered and washed the carbon cake with Chloroform. To the combined filtrate and washings was added methanol-HCl (1.1 molar equivalents) slowly added in about 10-15 minutes. Raised the temperature to 60-62° C. and maintained for 1 hour. Cooled to 25-30° C. and filtered the product and washed the cake with chloroform and dried to get 10.14 g (92.85% by theory) of Erlotinib monohydrochloride as a white solid.

Purity: 99.80% (by HPLC)

EXAMPLE 9

Preparation of Erlotinib Monohydrochloride

Into a 500 ml four necked round-bottomed flask equipped with a mechanical stirrer, reflux condenser and thermometer socket, are charged Acetonitrile (200 ml), Erlotinib base (10 g) and raised the temperature to 70-75° C. to get a clear solution. Activated carbon (2 g) was charged and maintained for 15-20 minutes. Filtered the reaction mass and washed the carbon cake with hot Acetonitrile. To the combined filtrate and washings were added isopropyl alcohol-HCl (1.1 molar equivalents) slowly added in about 10-15 minutes. Raised the temperature to 70-75° C. and maintained for 1 hour. Cooled the reaction mass to 25-30° C. and filtered the product and washed the cake with Acetonitrile and dried to get 10.25 g (93.86% by theory) of Erlotinib monohydrochloride as a white solid.

Purity: 99.83% (by HPLC)

Example 10

Preparation of Erlotinib Monohydrochloride

Into a 250 ml four necked round bottomed flask equipped with a mechanical stirrer, reflux condenser and thermometer socket, are charged Ethyl acetate (200 ml), Erlotinib base (10 g) and raised the temperature to 70-75° C. to get a clear solution. Activated carbon (2 g) was charged and maintained for 15-20 minutes. Filtered the reaction mass and washed the carbon cake with hot ethyl acetate. To the combined filtrate and washings was added isopropyl alcohol-HCl (1.1 molar equivalents) slowly added in about 10-15 minutes. Raised the temperature to 70-75° C. and maintained for 1 hour. Cooled to 25-30° C. and filtered the product and washed the cake with ethyl acetate and dried to get 10.2 g (93.4% by theory) of Erlotinib monohydrochloride as a white solid.

Purity: 99.82% (by HPLC)

EXAMPLE 11

Preparation of Erlotinib Monohydrochloride

Into a 250 ml four-necked round bottomed flask equipped with a mechanical stirrer, reflux condenser and thermometer socket, are charged Water (100 ml), Erlotinib base (10 g). To the suspension was added concentrated HCl (1.1 molar equivalents) slowly added in about 10-15 minutes. Maintained for 1 hour at 25-30° C. Filtered the product and washed the cake with Water and dried to get 10.25 g (93.9% by theory) of Erlotinib monohydrochloride as a white solid.

Purity: 99.81% (by HPLC)

Advantages of the Present Process:

(1) Present process does not require costly Platinum oxide.
(2) Present process uses simple raw materials like acetic anhydride, Hydrobromic acid, etc.
(3) Present process does not require any Chromatographic Purification.
(4) Erlotinib Hydrochloride obtained by this process is of high pure (99.8% by HPLC)
(5) Present process involves novel compounds of the formulae-12 & 13.

We claims:

1. A process for preparing Erlotinib [N-(3-ethynylphenyl)-6,7-bis(2-methoxy-ethoxy)-4-quinazolinamine] of formula (1),

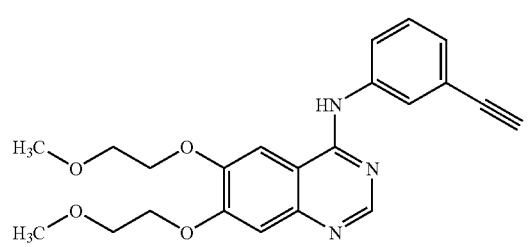
(1)

or a pharmaceutically acceptable salt thereof; the process comprising:

(i) reacting 6,7-dimethoxy-4(3H)-quinazolinone of formula (8)

(8)

with aqueous hydrobromic acid or pyridine hydrochloride to get a hydrobromide or hydrochloride salt and neutralizing with a base to get a compound of formula (9)

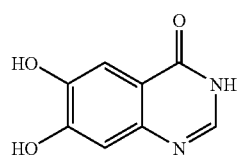
(9)

(ii) acylating the compound of formula (9) using acylating agent at a temperature of 20-150° C. and in the presence of a catalyst to get a bis-acylated derivative of formula (10);

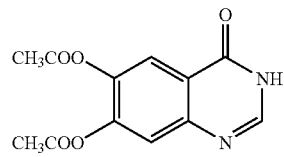
(10)

(iii) converting the compound of formula (10) into a leaving group 'X' by using an appropriate reagent in the presence or absence of a solvent at 10-100° C. to get a compound of formula (11)

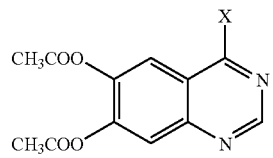
(11)

in which X is Halogen, OMs, OTs, or OBs;

(iv) condensing the reaction mixture containing the compound of formula (11) with 3-ethynylaniline in an organic solvent at 10-100° C. to get a compound of formula (12),

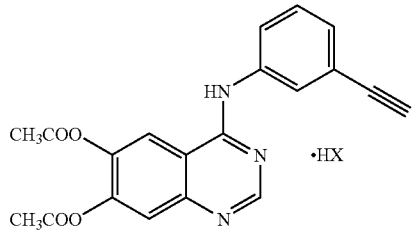
(12)

wherein X is halogen, OMs, OTs, or OBs;

(v) reacting the compound of formula (12) with a base at 20 to 60° C. to get a deacylated compound of formula (13),

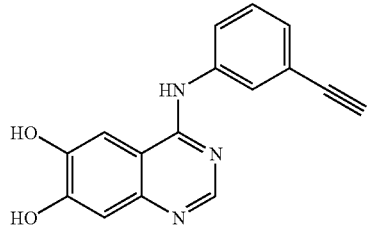
(13)

(vi) reacting the compound of formula (13) with a 2-halo-ethylmethyl ether in the presence of a base at 25-100° C. to get erlotinib base of the formula (1),

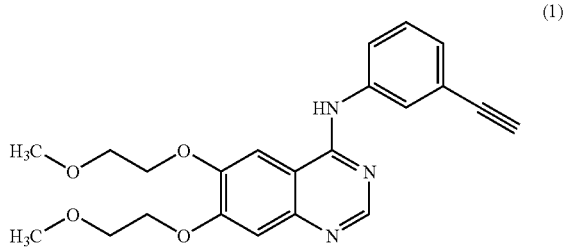

(1)

(vii) recrystallising the erlotinib base from (vi) to get purified erlotinib base.

2. A process as claimed in claim 1, wherein hydrobromic acid is used in (i).

3. A process as claimed in claim 2, wherein the hydrobromic acid used in (i) comprises aqueous hydrobromic acid that comprises 30-50% w/w hydrogen bromide.

4. A process as claimed in claim 1, wherein step (i) is carried out at a temperature at 80-150° C.

5. A process as claimed in claim 1, wherein the base used for neutralization of the hydrobromide or hydrochloride salt in (i) is an inorganic base or an organic base.

6. A process as claimed in claim 1, wherein neutralization in (i) brings the reaction mixture to a pH of 6.5-7.5.

7. A process as claimed in claim 1, wherein the acylating agent in (ii) comprises acetic anhydride or acetyl chloride.

8. A process as claimed in claim 1, wherein the acylation step in step (ii) is carried out at a temperature at 120-130° C.

9. A process as claimed in claim 1, wherein the catalyst used in (ii) comprises pyridine or 4-dimethylaminopyridine.

10. A process as claimed in claim 1, wherein the reagent used in (iii) comprises oxalyl chloride, thionyl chloride, phosphorous pentachloride, phosphorous oxychloride, methanesulfonyl chloride, benzenesulfonyl chloride, or para-toluene sulfonylchloride.

11. A process as claimed in claim 1, wherein (iii) employs a solvent, and the solvent used in (iii) and (iv) comprises chloroform, methylene chloride, toluene, acetonitrile, or cyclohexane.

12. A process as claimed in claim 1, wherein the temperature in (iii) and (iv) is 60-80° C.

13. A process as claimed in claim 1, wherein the base used in (v) comprises sodium hydroxide, potassium hydroxide, or aqueous ammonia solution in a lower alcohol.

14. A process as claimed in claim 1, wherein the temperature in (v) is 25-35° C.

15. A process as claimed in claim 1, wherein the 2-halo-ethylmethyl ether used in (vi) comprises 2-chloro-ethylmethyl ether, 2-bromo-ethylmethyl ether, or 2-iodo-ethylmethyl ether.

16. A process as claimed in claim 1, wherein the base used in (vi) comprises an inorganic base or an organic base.

17. A process as claimed in claim 1, wherein step (vi) employs a solvent, and the solvent comprises dimethylformamide, acetonitrile, tetrahydrofuran, acetone, dimethylacetamide, or isopropyl alcohol.

18. A process as claimed in claim 1, wherein step (vi) is carried out at 40-60° C.

19. A process as claimed in claim 1, wherein recrystallization in (vii) employs a solvent, the solvent comprising water, ethyl acetate, acetonitrile, isopropyl alcohol, methyl ethyl ketone, dimethylacetamide, or a mixture thereof.

20. A process as claimed in claim 1, wherein recrystallization in step (vii) is done at a temperature of 0-30° C.

21. A process as claimed in claim 1, wherein the purified erlotinib base obtained in (vii) is of purity greater than 99.5% by HPLC.

22. The process of claim 1, further comprising:
(viii) reacting the recrystalized Erlotinib base by dissolving or suspending in a solvent with hydrochloric acid or hydrogen chloride gas to get Erlotinib hydrochloride (Formula 1a):

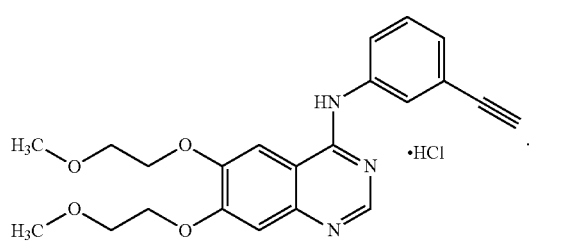

(1a)

23. The process of claim 22, wherein the solvent comprises an organic solvent, water, or a mixture thereof.

24. The process of claim 23, wherein the organic solvent comprises methanol, ethanol, or isopropanol.

25. The process of claim 22, further comprising isolating Erlotinib hydrochloride employing a temperature of 0-50° C.

26. The process of claim 22, further comprising isolating Erlotinib hydrochloride employing a temperature of 25-35° C.

27. The process of claim 22, wherein the erlotinib hydrochloride is of purity greater than 99.8% by HPLC.

28. The process of claim 4, wherein reacting in (i) is at 110-125° C.

29. The process of claim 15, wherein the 2-halo-ethylmethyl comprises 2-bromo-ethylmethyl ether or 2-iodo-ethylmethyl ether.

30. The process of claim 16, wherein the base employed in (vi) comprises sodium hydroxide, potassium hydroxide, hydrogen carbonate, carbonate, diisopropylethylamine, triethylamine, pyridine, 1,8-diaza-bicyclo [5.4.0]undec-7-ene (DBU), or 1,4-diazabicyclo[2.2.2]octane (DABCO).

31. The process of claim 19, wherein the solvent for recrystalizing comprises ethyl acetate, isopropyl alcohol, acetonitrile, or a mixture thereof.

* * * * *